United States Patent
Lagauche et al.

(10) Patent No.: US 10,596,560 B2
(45) Date of Patent: Mar. 24, 2020

(54) MODIFICATION OF A ZEOLITE OF TYPE EUO, AND ITS USE IN THE ISOMERIZATION OF AROMATIC C8 COMPOUNDS

(71) Applicant: IFP Energies nouvelles, Rueil-Malmaison (FR)

(72) Inventors: Matthieu Lagauche, Vernaison (FR); Laure Brandhorst, Lyons (FR); Christophe Bouchy, Lyons (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 205 days.

(21) Appl. No.: 14/909,637

(22) PCT Filed: Jun. 30, 2014

(86) PCT No.: PCT/FR2014/051671
§ 371 (c)(1),
(2) Date: Feb. 2, 2016

(87) PCT Pub. No.: WO2015/015077
PCT Pub. Date: Feb. 5, 2015

(65) Prior Publication Data
US 2016/0184809 A1   Jun. 30, 2016

(30) Foreign Application Priority Data

Aug. 2, 2013  (FR) .................................. 13 57715

(51) Int. Cl.
| | | |
|---|---|---|
| *B01J 29/06* | (2006.01) |
| *B01J 29/74* | (2006.01) |
| *B01J 37/00* | (2006.01) |
| *C07C 5/27* | (2006.01) |
| *B01J 29/72* | (2006.01) |
| *C01B 39/02* | (2006.01) |
| *B01J 29/70* | (2006.01) |
| *C10G 45/64* | (2006.01) |
| *C10G 45/62* | (2006.01) |
| *B01J 29/76* | (2006.01) |
| *B01J 29/78* | (2006.01) |
| *B01J 29/04* | (2006.01) |
| *B01J 35/10* | (2006.01) |

(Continued)

(52) U.S. Cl.
CPC ......... *B01J 29/7446* (2013.01); *B01J 29/045* (2013.01); *B01J 29/7023* (2013.01); *B01J 29/7073* (2013.01); *B01J 29/7246* (2013.01); *B01J 29/7646* (2013.01); *B01J 29/7846* (2013.01); *B01J 37/0009* (2013.01); *C01B 39/026* (2013.01); *C07C 5/2775* (2013.01); *C10G 45/62* (2013.01); *C10G 45/64* (2013.01); *B01J 29/043* (2013.01); *B01J 35/0066* (2013.01); *B01J 35/023* (2013.01); *B01J 35/10* (2013.01); *B01J 35/109* (2013.01); *B01J 35/1019* (2013.01); *B01J 35/1042* (2013.01); *B01J 35/1061* (2013.01); *B01J 2229/18* (2013.01); *B01J 2229/186* (2013.01); *B01J 2229/20* (2013.01); *B01J 2229/37* (2013.01); *B01J 2229/38* (2013.01); *B01J 2229/42* (2013.01); *C07C 2521/04* (2013.01); *C07C 2529/74* (2013.01); *C07C 2529/76* (2013.01); *C07C 2529/78* (2013.01); *C10G 2300/1096* (2013.01); *C10G 2400/30* (2013.01); *Y02P 20/52* (2015.11)

(58) Field of Classification Search
CPC ............... B01J 29/7246; B01J 29/7446; B01J 29/7023; B01J 29/043; B01J 29/7646; B01J 29/045; B01J 29/7846; B01J 29/7073; B01J 2229/18; B01J 2229/20; B01J 2229/37; B01J 2229/38; B01J 2229/42; B01J 2229/186; B01J 37/0009; B01J 35/023; B01J 35/10; B01J 35/109; B01J 35/1019; B01J 35/1042; B01J 35/1061; B01J 29/29; C01B 39/026; C07C 2529/74; C07C 2529/76; C07C 2529/78
USPC ...................... 502/63, 64, 66, 69, 73, 74, 85
See application file for complete search history.

(56) References Cited

U.S. PATENT DOCUMENTS

| | | | | |
|---|---|---|---|---|
| 4,467,129 A | * | 8/1984 | Iwayama | ................. B01J 29/80 585/481 |
| 4,482,773 A | * | 11/1984 | Chu | ...................... C07C 5/2724 502/62 |

(Continued)

FOREIGN PATENT DOCUMENTS

| | | |
|---|---|---|
| EP | 1013606 A1 | 6/2000 |
| EP | 1151964 A1 | 11/2001 |

(Continued)

OTHER PUBLICATIONS

Milina et al., "Decoupling porosity and compositional effects on desilicated ZSM-5 zeolites for optimal alkylation performance", Catal. Sci. Technol., 2012, 2, 759-766.*

(Continued)

*Primary Examiner* — Elizabeth D Wood
(74) *Attorney, Agent, or Firm* — Millen, White, Zelano and Branigan, P.C.

(57) ABSTRACT

A process is described for preparing a catalyst comprising at least one zeolite with a modified EUO structure type, at least one matrix and at least one metal from group VIII of the periodic classification of the elements. Said catalyst is used in a process for the isomerization of an aromatic feed comprising at least one compound containing eight carbon atoms per molecule.

13 Claims, No Drawings

(51) Int. Cl.
*B01J 35/02* (2006.01)
*B01J 35/00* (2006.01)

(56) References Cited

U.S. PATENT DOCUMENTS

| | | | |
|---|---|---|---|
| 6,051,129 A * | 4/2000 | Harris | C10G 45/64 208/135 |
| 6,471,938 B1 | 10/2002 | Vaughan et al. | |
| 7,893,309 B2 | 2/2011 | Guillon et al. | |
| 8,835,342 B2 * | 9/2014 | Ying | B01J 20/18 423/700 |
| 2008/0275281 A1 | 11/2008 | Guillon et al. | |
| 2011/0118107 A1 * | 5/2011 | Garcia-Martinez | B01J 29/04 502/62 |
| 2013/0037446 A1 | 2/2013 | Minoux et al. | |

FOREIGN PATENT DOCUMENTS

| | | | |
|---|---|---|---|
| FR | 2915112 A1 | 10/2008 | |
| FR | 2958297 A1 | 10/2011 | |

OTHER PUBLICATIONS

Groen et al., "Desilication: On the controlled generation of Mesoporosity in MFI zeolites", Jorunal of Materials Chemistry, 2006, 16, pp. 2121-2131.*
International Search Report for PCT/FR2014/051671 dated Sep. 8, 2014.
English Abstract of EP-1151964, Publication Date: Nov. 7, 2001.

* cited by examiner

MODIFICATION OF A ZEOLITE OF TYPE EUO, AND ITS USE IN THE ISOMERIZATION OF AROMATIC C8 COMPOUNDS

The present invention relates to a process for the preparation of a catalyst comprising a zeolite with a modified EUO structure type, at least one matrix and at least one metal from group VIII of the periodic classification of the elements. The invention also relates to the use of said catalyst prepared in accordance with the invention in a process for the isomerization of an aromatic cut comprising at least one aromatic compound containing eight carbon atoms per molecule for the production of para-xylene. This cut is usually known as an "aromatic C8 cut".

PRIOR ART

Catalysts used to carry out a process for the isomerization of aromatic compounds containing eight carbon atoms are generally zeolitic catalysts. ZSM-5, used alone or as a mixture with other zeolites, for example mordenite, is included among the zeolites used for the isomerization of an aromatic C8 cut. These catalysts have in particular been described in patents U.S. Pat. Nos. 4,467,129, 4,482,773 and EP B 0 013 617. The prior art catalysts, in particular catalysts based on mordenite zeolite, have mediocre catalytic performances as they give rise to side reactions which are not negligible. Examples of such secondary reactions which may be cited include naphthene ring opening, followed or otherwise by cracking (transformation into paraffins), or indeed disproportionation and transalkylation reactions of aromatics containing eight carbon atoms (transformation into unwanted aromatic compounds), or indeed the hydrogenation of aromatic compounds (transformation into naphthenes). Catalysts based on ZSM-5 zeolite, alone or as a mixture with other zeolites such as mordenite, have already been used and have not reached optimal catalytic performances for the conversion of ethylbenzene into xylenes.

Patent applications EP 0 923 987 A1 and WO 2005/065380 respectively propose a catalyst based on a zeolite with structure type EUO and with structure type MTW. Although these zeolitic catalysts provide an interesting selectivity for xylenes, their xylenes yield is too low.

Thus, there is still a need for the development of catalysts for the isomerization of aromatic C8 cuts into xylenes with improved performances in terms of selectivity and activity.

The activity of a catalyst is known to be improved by the creation of mesopores in and/or between the crystallites of the zeolite used (intra and/or extra-crystalline mesoporosity). Desilication of the zeolite in an alkaline medium constitutes one of the techniques which may be used to generate the mesoporosity. However, although that treatment is known to the skilled person, the operating conditions to be employed are specific to the particular characteristics of each zeolite (structure type, size and morphology of crystallites, Si/Al ratio, etc.). In the open literature, carrying out the desilication in an alkaline medium has been described for zeolites with structure type MFI, MTW, MOR, BEA, AST, FER, MWW, IFR, STF, CHA, FAU and TON (D. Verboekend, J. Perez-Ramirez, Catalysis Science and Technology, 2011, 1, 897-890), but none of the documents in the literature has described the alkaline treatment of a zeolite with structure type EUO.

The Applicant's research has led to the development of a novel process for the preparation of a novel catalyst comprising a zeolite with structure type EUO, more particularly an EU-1 zeolite, modified by a specific alkaline treatment. It has surprisingly been discovered that a catalyst in the form of beads or extrudates comprising at least one matrix, at least one metal from group VIII of the periodic classification of the elements and at least one EUO zeolite, more particularly an EU-1 zeolite which has undergone an alkaline treatment under the conditions described in the invention, results in improved catalytic performances for the isomerization of an aromatic feed when said catalyst is used in a process for the isomerization of an aromatic cut comprising at least one aromatic compound containing eight carbon atoms per molecule. A catalyst of this type is more active and more selective than a catalyst comprising an EUO zeolite which has not undergone the alkaline treatment of the invention, or which has undergone an alkaline treatment under conditions which differ from those described in the present invention. This results in an increase in the xylenes yield when the isomerization process is carried out in the presence of the catalyst of the invention.

DETAILED DESCRIPTION OF THE INVENTION

The present invention concerns a process for the preparation of a catalyst for the isomerization of an aromatic cut containing at least one aromatic compound containing eight carbon atoms per molecule, said catalyst comprising at least one modified EUO zeolite which has undergone an alkaline treatment, at least one matrix and at least one metal from group VIII of the periodic classification of the elements.

The process of the invention is a process for the preparation of a catalyst for the isomerization of an aromatic cut containing at least one aromatic compound containing eight carbon atoms per molecule from an initial zeolite with structure type EUO having an overall Si/Al atomic ratio in the range 5 to 100, said catalyst comprising at least one matrix and at least one metal from group VIII, said process comprising at least the following steps:

i) a step for desilication of said initial zeolite with structure type EUO by suspension in an alkaline solution with a normality in the range 0.1 to 3M, stirring at a stirring speed in the range 100 to 1000 rpm, and heating to a temperature in the range 40° C. to 100° C. for a period in the range 5 min to 24 h;

ii) a step for washing the zeolite obtained from step i) with distilled water;

iii) a step for preparation of a support by shaping said washed EUO zeolite obtained from step ii) with a matrix in a manner such that the percentage by weight of the zeolite is in the range 1% to 90% with respect to the weight of the support;

iv) at least one step for ion exchange of the washed zeolite obtained from step ii) or the support obtained from step iii) in a manner such as to eliminate at least a portion of the alkaline cation present in the cationic position in the zeolite;

v) a step for depositing at least one metal from group VIII of the periodic classification of the elements onto said exchanged zeolite obtained from step iv) or said exchanged support obtained from step iv) in a manner such that the percentage by weight of said metal is 0.01% to 4% with respect to the weight of the catalyst.

i) Desilication Step

The initial zeolite with initial structure type EUO used in the present invention may be selected from EU-1 zeolite, TPZ-3 zeolite and ZSM-50 zeolite; preferably, said zeolite is EU-1 zeolite.

EU-1, TPZ-3 and ZSM-50 zeolites with structure type EUO are well known in the prior art (Atlas of Zeolite Framework Types, Ch. Baerlocher, W. M. Meier, D. H. Olson, 5$^{th}$ edition, 2001). It is known that a zeolite with structure type EUO, in particular an EU-1 zeolite, has a mono-dimensional microporous framework with a pore diameter of 4.1×5.4 Å (1 Å=1 Angström=$10^{-10}$ m). Furthermore, in their article in the review Zeolites (1988, 8, 74), N. A. Briscoe et al. disclosed that these mono-dimensional channels have lateral pockets with a depth of 8.1 Å and diameter of 6.8×5.8 Å.

The initial zeolite with structure type EUO used in the present invention has an overall Si/Al atomic ratio in the range 5 to 100, preferably in the range 10 to 50 and highly preferably in the range 10 to 35. Said zeolite is advantageously composed of crystallites, preferably isotropic, with dimensions in the range 5 nm to 1 μm, preferably in the range 10 nm to 500 nm and more preferably in the range 20 nm to 100 nm. The initial zeolite used in the invention may be in the as-synthesized form (with an organic template) or calcined; preferably, said initial zeolite is in the calcined form.

The desilication step of the invention is carried out in an alkaline solution, preferably an aqueous alkaline solution. Said alkaline solution is advantageously an aqueous alkaline solution based on lithium hydroxide LiOH, sodium hydroxide NaOH, potassium hydroxide KOH or caesium hydroxide CsOH. The alkaline solution has a normality in the range 0.1 to 3 M, preferably in the range 0.5 to 2 M, more preferably in the range 0.7 to 1.5 M and still more preferably in the range 0.8 to 1.2 M.

Advantageously, the ratio between the volume (expressed in mL) of the alkaline solution used in desilication step i) and the mass of dry zeolite to be desilicated (expressed in g) is in the range 2 to 20, and preferably in the range 4 to 18. The mixture of the zeolite and the alkaline solution must be stirred with a stirring speed in the range 100 to 1000 rpm, preferably in the range 200 to 400 rpm, and heated to a temperature in the range 40° C. to 100° C., preferably in the range 50° C. to 100° C., more preferably in the range 50° C. to 90° C. and still more preferably in the range 60° C. to 90° C., for a period in the range 5 min to 24 h, preferably in the range 15 min to 10 h, more preferably in the range 15 min to 5 h and still more preferably in the range 30 min to 3 h.

ii) Washing Step

Following the desilication step i) resulting in the modified zeolite, the mixture is advantageously cooled to ambient temperature before carrying out washing step ii) of the preparation process of the invention.

The zeolite obtained from step i) is advantageously washed with distilled water between 2 and 10 times. The ratio between the volume of distilled water (mL) used and the mass of zeolite (g) is typically in the range 2 to 20, preferably in the range 4 to 18. The washed zeolite is advantageously separated by centrifuging, at a speed in the range 2000 to 14000 rpm, preferably in the range 5000 to 1000 rpm. Successive washes with distilled water may be carried out until a pH close to seven is obtained in the aqueous solution separated by centrifuging. The washed zeolite is optionally oven dried at a temperature in the range 60° C. to 130° C. for a period in the range 1 h to 24 h. The optionally dried zeolite may then undergo step iv) of the preparation process, namely the ion exchange step. In a variation of the process of the invention, said zeolite initially undergoes step iii) for shaping with a matrix such that the percentage by weight of the zeolite is in the range 1% to 90% with respect to the weight of support, before carrying out the ion exchange step iv).

Acid Treatment

Advantageously, in accordance with the invention, the washed EUO zeolite obtained from step ii) or the zeolite of the support obtained from step iii) undergoes an acid treatment by suspension in an acidic solution, preferably an aqueous acidic solution, before ion exchange step iv).

The acid treatment may be carried out with any dilute aqueous solution of a mineral or organic acid, such as hydrochloric acid HCl, phosphoric acid $H_3PO_4$, nitric acid $HNO_3$, citric acid $C_6H_8O_7$, acetic acid $C_2H_4O_2$ or indeed sulphuric acid $H_2SO_4$, having a normality in the range 0.001 to 2 M, preferably in the range 0.01 to 1.5 M, more preferably in the range 0.02 to 1 M and still more preferably in the range 0.05 to 0.8 M. Preferably, the acid treatment is carried out with a dilute aqueous solution of hydrochloric acid. The ratio between the volume of the aqueous solution used to carry out the acid treatment (mL) and the mass of washed and dried zeolite or the mass of the dried support (shaped zeolite) (g) is in the range 2 to 200, preferably in the range 5 to 150. The mixture is stirred at a stirring speed in the range 100 to 1000 rpm, preferably in the range 200 to 400 rpm, and heated to a temperature in the range 30° C. to 100° C., preferably in the range 40° C. to 90° C., more preferably in the range 45° C. to 85° C. and still more preferably in the range 50° C. to 80° C., for a period in the range 5 min to 24 h, preferably in the range 15 min to 10 h, more preferably in the range 30 min to 8 h and still more preferably in the range 45 min to 8 h. At the end of the acid treatment, the mixture is advantageously cooled to ambient temperature. The zeolite or the support obtained from this acid washing step is advantageously washed between 2 and 10 times with distilled water. The ratio between the volume of distilled water (mL) used and the mass of zeolite or support (g) is typically in the range 2 to 200, preferably in the range 5 to 150. The washed zeolite (acid washing) is advantageously separated by centrifuging at a speed in the range 2000 to 14000 rpm, preferably in the range 5000 to 1000 rpm. The washed support (acid washing) is advantageously separated by filtering. Successive washes with distilled water may be carried out until a pH close to seven is reached in the aqueous washing solution. The washed zeolite or the washed support (acid washing) are optionally oven dried at a temperature in the range 60° C. to 130° C. for a period in the range 1 h to 24 h.

iii) Preparation of Support

The catalyst is prepared by carrying out said support preparation step iii), also known as the step for shaping the washed zeolite obtained from step ii) with a matrix.

In order to carry out said step iii) for preparation of the support by shaping said washed zeolite with structure type EUO, preferably the washed EU-1 zeolite, obtained from step ii), a matrix is used for shaping, selected from clays, magnesia, aluminas, silicas, titanium oxide, boron oxide, zirconia, aluminum phosphates, titanium phosphates, zirconium phosphates, silica-aluminas and carbon, or a mixture of at least two of these compositions. Preferably, the matrix is an alumina.

The zeolite content in the support is in the range 1% to 90% by weight, preferably in the range 3% to 80% by weight and still more preferably in the range 4% to 60% by weight.

More particularly, preparation of the support in accordance with said step iii) consists of mixing the washed zeolite with structure type EUO, preferably washed EU-1 zeolite obtained from step ii), in a moist gel of matrix, preferably alumina, generally obtained by mixing at least one acid and a matrix powder, for a period necessary for obtaining good homogeneity in the paste, i.e. for about ten minutes, for example, then passing the paste obtained through a die to form extrudates, for example with a diameter of 0.4 to 4 mm. Beads may also be obtained by a granulation technique. Shaping is generally followed by drying then by calcining. Drying is advantageously carried out at a temperature in the range 100° C. to 150° C. for a period in the range 5 to 20 h in an oven. Calcining is advantageously carried out at a temperature in the range 250° C. to 600° C. for a period in the range 1 to 8 h.

iv) Ion Exchange Step

In accordance with the invention, the washed zeolite obtained from step ii) or the support obtained from step iii) undergoes one or more ion exchanges in order to eliminate at least a portion of the alkaline cation present in the cationic position in the zeolite.

An aqueous solution containing an ammonium precursor such as ammonium nitrate $NH_4NO_3$, ammonium acetate $CH_3COONH_4$, tetrapropylammonium hydroxide $C_{12}H_{27}NO$, tetramethylammonium hydroxide $C_4H_{13}NO$ or tetraethylammonium hydroxide $C_8H_{21}NO$ with a normality in the range 0.2 to 12 M may be used to carry out exchange step iv). The ratio between the volume of the aqueous solution used to carry out the exchange (mL) and the mass of dry zeolite or dry support to be exchanged (g) is in the range 2 to 20, and preferably in the range 5 to 15. The solid is poured into a flask or an Erlenmeyer flask which contains an aqueous solution with the ammonium precursor. The mixture is stirred and optionally heated to a temperature in the range 50° C. to 100° C. for a period in the range 2 to 10 hours. The solution is then advantageously removed and the solid is rinsed with distilled water between 2 and 10 times then optionally oven dried at a temperature in the range 60° C. to 130° C. for a period in the range 1 to 24 h. The exchange step may be repeated several times in order to substantially eliminate all alkaline cations which may be present in the cationic position in the zeolite. The solid obtained is then advantageously calcined for a period in the range 1 to 24 h, preferably in dry air, at a temperature in the range 300° C. to 600° C., preferably in the range 450° C. to 550° C., in a quartz reactor equipped with a frit in its center, with the gas moving from bottom to top at a flow rate in the range 0.5 L/h/g of solid to 3 L/h/g of solid.

Highly advantageously, the zeolite with modified structure type EUO present in the catalyst of the invention is in its protonated form (hydrogen $H^+$ form). Preferably, the alkaline cation content in said zeolite in its protonated form is less than 3000 ppm by weight.

v) Metal Deposition Step

Step v) for preparing the catalyst consists of depositing at least one metal from group VIII of the periodic classification of the elements onto said exchanged zeolite obtained from step iv) or said exchanged support obtained from step iv) in a manner such that the percentage by weight of said metal is 0.01% to 4%, preferably 0.05% to 2% with respect to the final catalyst weight.

In accordance with the invention, said catalyst comprises at least one metal from group VIII selected from iron, cobalt, nickel, ruthenium, rhodium, palladium, osmium, iridium and platinum, preferably selected from noble metals from group VIII, highly preferably selected from palladium and platinum, and still more preferably, platinum.

The dispersion of the metal(s) from group VIII, determined by chemisorption, for example by $H_2$—$O_2$ titration or by carbon monoxide chemisorption, is in the range 50% to 100%, preferably in the range 60% to 100% and still more preferably in the range 70% to 100%. The macroscopic distribution coefficient of the metal(s) from group VIII, obtained from its profile determined using a Castaing microprobe, defined as the ratio of the concentrations of the metal(s) from group VIII at the core of the grain with respect to the boundary of that same grain, is in the range 0.7 to 1.3, preferably in the range 0.8 to 1.2. The value of this ratio, close to 1, is evidence of the homogeneity of the distribution of the metal(s) from group VIII in the catalyst.

The catalyst optionally further comprises at least 0.01% to 2%, preferably 0.05% to 1% by weight with respect to the weight of the final catalyst, of an additional metal selected from the group formed by metals from groups IIIA, IVA and VIIB of the periodic classification of the elements, and preferably selected from gallium, indium, tin and rhenium. Said additional metal is preferably selected from indium, tin and rhenium.

In order to deposit the metal from group VIII of the periodic classification of the elements, any deposition technique known to the skilled person and any precursor of such metals may be suitable.

When the metal(s) is(are) deposited on the support, controlling various parameters utilized during deposition, in particular the nature of the precursor of the metal(s) from group VIII used, means that the deposition of said metal(s) can be orientated primarily onto the matrix or onto the modified zeolite.

Thus, in order to introduce the metals from group VIII, preferably platinum and/or palladium, primarily onto the matrix, anion exchange may be carried out with hexachloroplatinic acid and/or hexachloropalladic acid, in the presence of a competing agent, for example hydrochloric acid, deposition generally being carried out following a calcining step, for example at a temperature in the range 350° C. to 550° C. and for a period in the range 1 to 4 hours. With precursors of this type, the metal(s) from group VIII is(are) deposited primarily on the matrix and said metal(s) have a good dispersion and a good macroscopic distribution through the grain of the catalyst.

It is also possible to envisage depositing the metal(s) from group VIII, preferably platinum and/or palladium, by cationic exchange in a manner such that said metal(s) are primarily deposited on the modified zeolite. Thus, in the case of platinum, the precursor may, for example, be selected from ammoniacal compounds such as salts of platinum (II) tetramines with formula $Pt(NH_3)_4X_2$, salts of platinum (IV) hexamines with formula $Pt(NH_3)_6X_4$; salts of platinum (IV) halogenopentamines with formula $(PtX(NH_3)_5)X_3$; salts of platinum N-tetrahalogenodiamines with formula $PtX_4(NH_3)_2$; and halogenated salts with formula $H(Pt(acac)_2X)$; X being a halogen selected from the group formed by chlorine, fluorine, bromine and iodine, X preferably being chlorine, and "acac" representing the acetylacetonate group (with empirical formula $C_5H_7O_2$), a derivative of acetylacetone. With precursors of this type, the metal(s) from group VIII is(are) deposited primarily on the zeolite and said metal(s) have a good dispersion and a good macroscopic distribution through the catalyst grain.

Dry impregnation of the metal from group VIII onto the shaped zeolite (support) results in said metal being deposited both on the matrix and on the metal zeolite.

In the case in which the catalyst of the invention also contains at least one metal selected from metals from groups IIIA, IVA and VIIB, any of the techniques for depositing a metal of this type which are known to the skilled person and any precursors of such metals may be suitable.

It is possible to add the metal(s) from group VIII and that (those) from groups IIIA, IVA and VIIB either separately or simultaneously in at least one unitary step. When at least one metal from groups IIIA, IVA and VIIB is added separately, it is preferably added after the metal from group VIII.

The additional metal selected from metal from groups IIIA, IVA and VIIB may be introduced via compounds such as, for example, chlorides, bromides and nitrates of metals from groups IIIA, IVA and VIIB. As an example in the case of indium, the nitrate or the chloride may advantageously be used, and in the case of rhenium, perrhenic acid is advantageously used. The additional metal selected from metals from groups IIIA, IVA and VIIB may also be introduced in the form of at least one organic compound selected from the group constituted by complexes of said metal, in particular polyketone complexes of the metal and hydrocarbyl metals such as metal alkyls, cycloalkyls, aryls, alkylaryls and arylalkyls. In this latter case, the metal is advantageously introduced with the aid of a solution of an organometallic compound of said metal in an organic solvent. It is also possible to employ organohalogenated compounds of the metal. Particular examples of organometallic compounds which may be cited are tetrabutyl tin in the case of tin, and triphenyl indium in the case of indium.

If the additional metal selected from metals from groups IIIA, IVA and VIIB is introduced before the metal from group VIII, the compound of the metal from group IIIA, IVA and/or VIIB used is generally selected from the group constituted by the metal halide, nitrate, acetate, tartrate, carbonate and oxalate. The introduction is advantageously carried out in aqueous solution. However, it may also be introduced with the aid of a solution of an organometallic compound of a metal, for example tetrabutyl tin. In this case, before proceeding with introducing at least one metal from group VIII, calcining is carried out in air.

In addition, intermediate treatments such as calcining and/or reduction, for example, may be applied between successive depositions of the various metals.

Prior reduction of the final catalyst ex situ, in a stream of hydrogen, may be carried out, for example at a temperature of 450° C. to 600° C., for a period of 0.5 to 4 h (hours).

The catalyst optionally comprises sulphur in a quantity such that the ratio of the number of atoms of sulphur to the number of atoms of metal(s) from group VIII is in the range 0.5 to 2.

In the case in which the catalyst does not contain sulphur, a reduction of the metal in hydrogen is carried out in situ before injecting the feed.

In the case in which the catalyst of the invention contains sulphur, the sulphur is introduced onto the shaped catalyst, which has been calcined, containing the metal or metals mentioned above, either in situ before the catalytic reaction, or ex situ. Any sulphurization is carried out after reduction. In the case of an in situ sulphurization, if the catalyst has not already been reduced, reduction is carried out before the sulphurization. In the case of ex situ sulphurization, reduction is carried out followed by sulphurization. Sulphurization is carried out in the presence of hydrogen using any sulphurization agent which is well known to the skilled person, such as dimethyl sulphide or hydrogen sulphide, for example. As an example, the catalyst is treated with a feed containing dimethyl sulphide in the presence of hydrogen, with a concentration such that the sulphur/metal atomic ratio is 1.5. The catalyst is then maintained for approximately 3 hours at approximately 400° C. in a flow of hydrogen before injecting the feed.

Characterization Techniques

The overall Si/Al atomic ratio of the initial EU-1 zeolite is measured by X ray fluorescence. X ray fluorescence is a general elementary analysis technique which can be used to analyse all of the elements of the periodic table starting from boron. It is possible to assay from just a few ppm (parts per million) up to 100%. In this invention, this technique was used to assay the silicon and aluminum in the zeolite (as a percentage by weight) and thus could be used to calculate the Si/Al atomic ratio. XRF analyses of the aluminum and silicon were carried out on powder using a Thermofischer Scientific Advant-X instrument.

The sodium content in the various zeolites in their protonated form (after the ion exchange steps) was measured by atomic absorption spectrometry or optical emission spectrometry. The sodium content was determined using an optical emission spectrometer (ICP-OES) SPECTRO, ARCOS SOP.

The textural properties of the initial EUO zeolite and the modified EUO zeolites were measured by nitrogen adsorption/desorption at −196° C. The specific surface area was calculated using the BET method. The microporous volume ($V_{micro}$) as well as the external surface area ($S_{ext}$) were obtained using a "t-plot" method, the statistical thickness being calculated using the Harkins and Jura formula. The mesoporous volume ($V_{meso}$) was obtained by subtracting the microporous volume from the total pore volume. The term "total pore volume" means the volume of nitrogen adsorbed at a relative nitrogen pressure ($P/P_0$) of 0.95. The adsorption-desorption isotherm measurements for the samples were carried out on a Micromeritics ASAP 2024 porosimeter. The operation for degassing the solids was carried out previously using a pre-treatment bay. Degassing was carried out by heating in two stages: a first constant temperature stage lasting 2 h at 100° C., followed by a second constant temperature stage lasting 6 h, at 500° C.; the temperature ramp-up rates were approximately twenty degrees Celsius per minute.

The X ray diffraction technique was employed in order to verify whether the crystallographic structure of the zeolite used was indeed present in the various samples. This was carried out by comparing the experimental diffractogram with the theoretical diffractogram (file number JCPDS 04-007-2506). The analyses were carried out on a PANanytical X'Pert PRO MPD θ-θ, using the Kα line of copper ($\lambda$=1.5402 Å) and an X'celerator detector. During the analysis, the scan was carried out between 2° and 72° at ambient temperature in 0.02° steps and with a measurement period of 6 seconds per step.

Transmission electron microscopy (TEM) was used to evaluate the typical dimensions of the zeolite crystallites. The TEM observations were carried out using a JEOL 21000F—FEG (Field Emission Gun) microscope with an acceleration voltage of 200 kV.

Using a Catalyst in the Process for the Isomerization of Aromatic C8 Cuts

The present invention also pertains to a process for the isomerization of a cut containing at least one aromatic compound containing eight carbon atoms per molecule, said process comprising bringing said aromatic cut into contact with at least said catalyst in accordance with the invention.

In particular, said aromatic cut containing at least one aromatic compound containing eight carbon atoms per molecule comprises, as the aromatic compound containing eight carbon atoms per molecule, either uniquely a mixture of xylenes or uniquely ethylbenzene, or a mixture of xylene(s) and ethylbenzene.

Said isomerization process is generally carried out in accordance with the following operating conditions: a temperature of 300° C. to 500° C., preferably 320° C. to 450° C. and more preferably 340° C. to 430° C.; a partial pressure of hydrogen or 0.3 to 1.5 MPa, preferably 0.4 to 1.2 MPa and more preferably 0.7 to 1.2 MPa; a total pressure of 0.45 to 1.9 MPa, preferably 0.6 to 1.5 MPa; and a feed space velocity, expressed in kilograms of feed (aromatic cut) introduced per kilogram of catalyst per hour, of 0.25 to 30 $h^{-1}$, preferably 1 to 10 $h^{-1}$ and still more preferably 2 to 6 $h^{-1}$.

The following examples illustrate the invention without, however, limiting its scope.

Example 1 (not in Accordance with the Invention): Preparation of an EU-1 Zeolite An EU-1 zeolite was synthesized in accordance with the disclosure in patent EP B1 0 042 226 using the organic template 1,6 N,N,N,N',N',N'-hexamethylhexamethylene diammonium. To prepare a zeolite of this type, the reaction mixture had the following molar composition: 60 $SiO_2$:10.6 $Na_2O$:5.27 NaBr:1.5 $Al_2O_3$:19.5 Hexa-$Br_2$:2777 $H_2O$. Hexa-$Br_2$ is 1,6 N,N,N,N',N',N'-hexamethylhexamethylene diammonium, with bromine being the counter-ion. The reaction mixture was placed in an autoclave and stirred (300 rpm) for 5 days at 180° C.

This EU-1 zeolite firstly underwent calcining known as dry calcining at 550° C. in a stream of dry air for 10 hours in order to eliminate the organic template. The solid was then placed under reflux for 4 hours in a solution of ammonium nitrate (100 mL of solution per gram of solid, concentration of ammonium nitrate 10 M) in order to exchange the alkaline cations with ammonium ions. This exchange step was carried out four times. The solid was then calcined at 550° C. for 4 h in a tube furnace. The solid so obtained was given the reference EU-1(1) and had a Si/Al atomic ratio of 15 and a sodium content of 73 ppm. Analysis by X ray diffraction confirmed that the EU-1 zeolite had indeed been obtained. Transmission electron microscopy demonstrated the presence of crystallites with a typical dimension in the range 20 to 80 nm, these crystallites forming agglomerates. Said EU-1(1) zeolite was analyzed by nitrogen porosimetry in order to determine its textural characteristics (Table 1).

Example 2 (in Accordance with the Invention): Preparation of a Modified EU-1 Zeolite The EU-1(1) zeolite was placed in a reflux flask, equipped with a mechanical stirrer where it underwent an alkaline treatment under the following conditions:
treatment temperature: 85° C.,
concentration of sodium hydroxide in the aqueous solution: 1 M,
treatment duration: 45 minutes,
ratio of volume of solution/mass of EU-1(1): 15 mL/g,
speed of mechanical stirrer: 330 rpm.

The modified zeolite was then washed three times with distilled water and separated by centrifuging (8000 rpm), then oven dried at 110° C. for 12 h. At the end of this alkaline treatment, a modified zeolite denoted EU-1(2) was obtained which was in its sodium form. The solid was placed under reflux for 4 hours in a solution of ammonium nitrate (100 mL of solution per gram of solid, concentration of ammonium nitrate 10 M) in order to exchange the alkaline cations for ammonium ions. This exchange step was carried out five times. The solid was then calcined at 550° C. for 4 h in a tube furnace. The zeolite was then in its protonated form and was denoted zeolite EU-1(3). The sodium content of the zeolite was 95 ppm and X ray diffraction analysis confirmed that the characteristic diffraction peaks of the EU-1 zeolite were still present. Said zeolite EU-1(3) was analyzed by nitrogen porosimetry in order to determine its textural characteristics (Table 1).

Example 3 (in Accordance with the Invention): Preparation of a Modified EU-1 Zeolite The EU-1(2) zeolite obtained in Example 2 was placed in a flask where it underwent an acid treatment under the following conditions:
treatment temperature: 65° C.,
concentration of hydrochloric acid in the aqueous solution: 0.1 M,
treatment duration: 360 minutes,
ratio of volume of solution/mass of EU-1(2): 100 mL/g,
speed of mechanical stirrer: 330 rpm.

The zeolite was then washed three times with distilled water and separated by centrifuging (8000 rpm), then oven dried at 110° C. for 12 h.

At the end of this acid treatment, a modified zeolite denoted EU-1(4) was obtained. The solid was placed under reflux for 4 hours in a solution of ammonium nitrate (100 mL of solution per gram of solid, concentration of ammonium nitrate 10 M) in order to exchange the alkaline cations for ammonium ions. This exchange step was carried out five times. The solid was then calcined at 550° C. for 4 h in a tube furnace. The zeolite was then in its protonated form and was denoted zeolite EU-1(5). The sodium content of said zeolite was 70 ppm and X ray diffraction analysis confirmed that the characteristic diffraction peaks of the EU-1 zeolite were still present. Said zeolite EU-1(5) was analyzed by nitrogen porosimetry in order to determine its textural characteristics (Table 1).

Example 4 (not in Accordance with the Invention): Preparation of a Modified EU-1 Zeolite The EU-1(1) zeolite was placed in a reflux flask equipped with a mechanical stirrer where it underwent an alkaline treatment under the following conditions:
treatment temperature: 65° C.,
concentration of sodium hydroxide in the aqueous solution: 0.05 M,
treatment duration: 60 minutes,
ratio of volume of solution/mass of EU-1(1): 15 mL/g,
speed of mechanical stirrer: 330 rpm.

The modified zeolite was then washed three times with distilled water and separated by centrifuging (8000 rpm), then oven dried at 110° C. for 12 h.

At the end of this alkaline treatment, a modified zeolite denoted EU-1(6) was obtained which was in its sodium form. The solid was placed under reflux for 4 hours in a solution of ammonium nitrate (100 mL of solution per gram of solid, concentration of ammonium nitrate 10 M) in order to exchange the alkaline cations for ammonium ions. This exchange step was carried out five times. The solid was then calcined at 550° C. for 4 h in a tube furnace. The zeolite was then in its protonated form and was denoted zeolite EU-1(7); its sodium content was 92 ppm. Analysis by X ray diffraction confirmed that the characteristic diffraction peaks of the EU-1 zeolite were still present. Said zeolite EU-1(7) was analyzed by nitrogen porosimetry in order to determine its textural characteristics (Table 1).

Table 1 presents the textural characteristics of the zeolites EU-1(1) (parent) and modified EU-1, EU-1(3), EU-1(5) and EU-1(7) determined from the nitrogen adsorption isotherms. The comparison of the textural properties of the parent EU-1 zeolite EU-1(1) with the zeolite EU-1(7) shows that carrying out an alkaline treatment on the EU-1 zeolite under conditions which were not in accordance with the invention did not allow the external surface area of the parent zeolite to be significantly developed, nor did it increase the mesoporous volume. In contrast, carrying out an alkaline treatment under conditions in accordance with the invention (EU-1(3)) meant that the external surface area was increased from 35 m²/g to 94 m²/g and the mesoporous volume was increased from 0.24 to 0.41 mL/g. Carrying out an acid treatment consecutive upon an alkaline treatment under conditions in accordance with the invention (EU-1(5)) further increased the external surface area (to obtain a value of 160 m²/g) as well as the mesoporous volume (to obtain a value of 0.59 mL/g). In addition, the acid treatment allowed the microporosity to be liberated, with the microporous volume reaching a value of 0.103 mL/g as opposed to 0.004 mL/g for the solid which had undergone an alkaline treatment but not then treated with acid (EU-1(3)).

TABLE 1

Textural characteristics of zeolites EU-1(1) (parent) and modified EU-1 EU-1 (3), EU-1 (5) and EU-1 (7).

| Reference for zeolite | $S_{BET}$ (m²/g) | $S_{ext}$ (m²/g) | $V_{meso}$ (mL/g) | $V_{micro}$ (mL/g) |
|---|---|---|---|---|
| EU-1(1) (parent) | 456 | 35 | 0.24 | 0.150 |
| EU-1(3) | 103 | 94 | 0.41 | 0.004 |
| EU-1(5) | 398 | 160 | 0.59 | 0.103 |
| EU-1(7) | 175 | 39 | 0.21 | 0.061 |

Example 5 (not in Accordance with the Invention): Preparation of Catalyst A Comprising an Unmodified EU-1 Zeolite The zeolite EU-1(1) (parent) from Example 1 was mixed with an SB3 type alumina gel provided by Condéa-Sasol. The mixed paste was extruded through a 1.4 mm die. After oven drying overnight at 110° C., the extrudates were calcined at 500° C. for two hours (temperature ramp-up 5° C./min) in a flushed bed in dry air (2 NL/h/g of solid). The extrudates then underwent anionic exchange with hexachloroplatinic acid in the presence of hydrochloric acid as the competing agent, in order to deposit 0.5% by weight of platinum with respect to the weight of catalyst. The moist solid was then dried at 120° C. for 12 hours and calcined in a flow of dry air at a temperature of 500° C. for one hour.

Catalyst A obtained contained, by weight, 10% of zeolite EU-1(1), 89.5% of alumina and 0.5% of platinum.

Example 6 (in Accordance with the Invention): Preparation of Catalyst B Comprising a Modified EU-1 Zeolite The zeolite EU-1(3) (parent) from Example 2 was mixed with an SB3 type alumina gel provided by Condéa-Sasol. The mixed paste was extruded through a 1.4 mm die. After oven drying overnight at 110° C., the extrudates were calcined at 500° C. for two hours (temperature ramp-up 5° C./min) in a flushed bed in dry air (2 NL/h/g of solid). The extrudates then underwent anionic exchange with hexachloroplatinic acid in the presence of hydrochloric acid as the competing agent, in order to deposit 0.5% by weight of platinum with respect to the weight of catalyst. The moist solid was then dried at 120° C. for 12 hours and calcined in a flow of dry air at a temperature of 500° C. for one hour.

Catalyst B obtained thereby contained, by weight, 10% of modified EU-1(3) zeolite, 89.5% of alumina and 0.5% of platinum.

Example 7 (in Accordance with the Invention): Preparation of Catalyst C Comprising a Modified EU-1 Zeolite The zeolite EU-1(5) from Example 3 was mixed with an SB3 type alumina gel provided by Condéa-Sasol. The mixed paste was extruded through a 1.4 mm die. After oven drying overnight at 110° C., the extrudates were calcined at 500° C. for two hours (temperature ramp-up 5° C./min) in a flushed bed in dry air (2 NL/h/g of solid). The extrudates then underwent anionic exchange with hexachloroplatinic acid in the presence of hydrochloric acid as the competing agent, in order to deposit 0.5% by weight of platinum with respect to the weight of catalyst. The moist solid was then dried at 120° C. for 12 hours and calcined in a flow of dry air at a temperature of 500° C. for one hour.

Catalyst C obtained thereby contained, by weight, 10% of modified EU-1(5) zeolite, 89.5% of alumina and 0.5% of platinum.

Example 8 (not in Accordance with the Invention): Preparation of Catalyst D Comprising a Modified EU-1 Zeolite The zeolite EU-1(7) from Example 4 was mixed with an SB3 type alumina gel provided by Condéa-Sasol. The mixed paste was extruded through a 1.4 mm die. After oven drying overnight at 110° C., the extrudates were calcined at 500° C. for two hours (temperature ramp-up 5° C./min) in a flushed bed in dry air (2 NL/h/g of solid). The extrudates then underwent anionic exchange with hexachloroplatinic acid in the presence of hydrochloric acid as the competing agent, in order to deposit 0.5% by weight of platinum with respect to the weight of catalyst. The moist solid was then dried at 120° C. for 12 hours and calcined in a flow of dry air at a temperature of 500° C. for one hour.

Catalyst D obtained thereby contained, by weight, 10% of modified EU-1(7) zeolite, 89.5% of alumina and 0.5% of platinum.

Example 9: Evaluation of the Catalytic Properties of Catalysts A, B, C and D in the Isomerization of Ethylbenzene The feed, constituted solely by ethylbenzene, was isomerized over various catalysts in a flushed bed in a reactor operating under isothermal conditions and with hydrogen being lost. The catalytic properties of the catalysts A, B, C and D were evaluated in succession for the isomerization of ethylbenzene. Before the catalytic test, each catalyst underwent a reduction step in a flow of hydrogen under the following operating conditions:
  total pressure: 1.3 MPa;
  hydrogen flow rate: 4 NL/h/g of catalyst;
  temperature ramp-up from ambient temperature to 450° C. at 10° C./minute;
  constant temperature stage for one hour at 450° C.;

temperature ramp-up from 450° C. to 480° C. at 5° C./min;

constant temperature stage of two hours at 480° C.

After the reduction step, the temperature and pressure were adjusted to the target test values and the ethylbenzene feed was injected. The operating conditions for isomerization were as follows:

temperature: 400° C.;
total pressure: 1 MPa;
partial pressure of hydrogen: 0.8 MPa;
feed: ethylbenzene;
feed space velocity, expressed in kilograms of feed introduced per kilogram of catalyst per hour, equal to 10 h$^{-1}$.

The catalysts were evaluated in terms of ethylbenzene conversion and selectivity for xylenes.

The selectivity for xylenes was calculated using the yield of xylenes produced. The xylenes yield was determined from the percentage by weight of xylenes produced, obtained by in-line analysis of each effluent using gas phase chromatography (FID detector).

The ethylbenzene conversion was the percentage of ethylbenzene consumed.

TABLE 2

Conversion of ethylbenzene and selectivity for xylenes over catalysts A, B, C and D after 4000 minutes of reaction

|  | Catalyst A | Catalyst B | Catalyst C | Catalyst D |
| --- | --- | --- | --- | --- |
| Ethylbenzene conversion (%) | 20.0 | 27.1 | 35.2 | 20.1 |
| Selectivity for xylenes (%) | 68.1 | 68.3 | 71.1 | 68.2 |
| Yield of xylenes (%) | 13.6 | 18.5 | 25.0 | 13.7 |

The results presented in Table 1 show that catalysts B and C each comprising an EU-1 zeolite modified in accordance with the process described in the invention, resulted in much better catalytic performances in terms of ethylbenzene conversion than those obtained using catalyst A which comprised an unmodified EU-1 zeolite and using catalyst D which comprised an EU-1 zeolite modified using a process which was not in accordance with the invention. Catalysts B and C in accordance with the invention are thus much more active than prior art catalyst A and than catalyst D. Furthermore, catalysts B and C in accordance with the invention have selectivities which are substantially comparable with those of catalysts A and D. As a consequence, catalysts B and C in accordance with the invention result in a far superior yield of xylenes than the yields of xylenes obtained with the comparative catalysts A and D.

The invention claimed is:

1. A process for the preparation of a catalyst product suitable for the isomerization of an aromatic cut containing at least one aromatic compound containing eight carbon atoms per molecule, said process comprising producing said catalyst product starting from an initial zeolite with structure type EUO having an overall Si/Al atomic ratio in the range 5 to 100, said catalyst product comprising at least one matrix and at least one metal from group VIII, said process comprising at least the following:

i) desilication of said initial zeolite with structure type EUO by suspension in an alkaline solution of lithium hydroxide LiOH, sodium hydroxide NaOH, potassium hydroxide KOH or caesium hydroxide CsOH with a normality of 0.5 to 2N, stirring at a stirring speed in the range 100 to 1000 rpm, and heating to a temperature in the range 40° C. to 100° C. for a period in the range 5 min to 24 h;

ii) washing the zeolite obtained from i) with distilled water;

iii) preparing a support by shaping said washed EUO zeolite obtained from ii) with a matrix in a manner such that the percentage by weight of the zeolite is in the range 1% to 90% with respect to the weight of the support;

iv) at least one ion exchange of the washed zeolite obtained from ii) or the support obtained from iii) in a manner such as to eliminate at least a portion of the alkaline cation present in the cationic position in the zeolite;

v) depositing at least one metal from group VIII of the periodic classification of the elements onto exchanged zeolite obtained from iv) or exchanged support obtained from iv) in a manner such that the percentage by weight of said metal is 0.01% to 4% with respect to the weight of the catalyst.

2. The process according to claim 1, in which the initial zeolite with structure type EUO is EU-1 zeolite, TPZ-3 zeolite or ZSM-50 zeolite.

3. The process according to claim 1, in which said initial zeolite is in the calcined form.

4. The process according to claim 1, in which said alkaline solution is an aqueous alkaline solution of lithium hydroxide LiOH, sodium hydroxide NaOH, potassium hydroxide KOH.

5. The process according to claim 1, in which washed EUO zeolite obtained from ii) or the zeolite of the support obtained from iii) undergoes an acid treatment by suspension in an acidic solution before the ion exchange iv).

6. The process according to claim 1, in which the matrix shaped with the support is clays, magnesia, aluminas, silicas, titanium oxide, boron oxide, zirconia, aluminium phosphates, titanium phosphates, zirconium phosphates, silica-aluminas and carbon, or a mixture of at least two there.

7. The process according to claim 1, in which the metal from group VIII is iron, cobalt, nickel, ruthenium, rhodium, palladium, osmium, iridium or platinum.

8. The process according to claim 1, in which the catalyst further comprises at least 0.01% to 2% by weight of an additional metal from groups IIIA, IVA or VIM of the periodic classification of the elements.

9. The process according to claim 5, wherein the acidic solution is an aqueous acidic solution.

10. The process according to claim 1, wherein the alkaline solution has a normality of 0.7 to 1.5N.

11. The process according to claim 1, wherein the alkaline solution has a normality of 0.8 to 1.2N.

12. The process according to claim 1, wherein the alkaline solution has a normality of 1 to 2N.

13. The process according to claim 12, wherein the alkaline solution is CsOH.

* * * * *